United States Patent
Seshadri et al.

(10) Patent No.: US 9,452,271 B2
(45) Date of Patent: Sep. 27, 2016

(54) NEBULIZER SYSTEMS AND METHODS

(71) Applicant: General Electric Company, Schenectady, NY (US)

(72) Inventors: Satyanarayanan Seshadri, Bangalore (IN); Marko Klaus Baller, Riegelsberg (DE); Dinesh Rakwal, Bangalore (IN)

(73) Assignee: General Electric Company, Schenectady, NY (US)

( * ) Notice: Subject to any disclaimer, the term of this patent is extended or adjusted under 35 U.S.C. 154(b) by 488 days.

(21) Appl. No.: 13/904,231

(22) Filed: May 29, 2013

(65) Prior Publication Data
US 2014/0352689 A1    Dec. 4, 2014

(51) Int. Cl.
| | | |
|---|---|---|
| A61M 15/00 | (2006.01) | |
| A61M 11/00 | (2006.01) | |
| B05B 17/06 | (2006.01) | |
| A61M 16/00 | (2006.01) | |

(52) U.S. Cl.
CPC ..... *A61M 15/0085* (2013.01); *A61M 15/0028* (2013.01); *A61M 11/005* (2013.01); *A61M 2016/0027* (2013.01); *A61M 2016/0033* (2013.01); *B05B 17/06* (2013.01)

(58) Field of Classification Search
CPC ......... A61M 11/005; A61M 2205/12; A61M 2205/126; B05B 17/06; B05B 17/0607; B05B 17/0615; B05B 17/0638; B05B 17/0646; B05B 17/0676
See application file for complete search history.

(56) References Cited

U.S. PATENT DOCUMENTS

| | | | | |
|---|---|---|---|---|
| 4,850,534 A | * | 7/1989 | Takahashi | B05B 17/063 239/102.2 |
| 5,152,456 A | | 10/1992 | Ross | |
| 5,312,281 A | | 5/1994 | Takahashi | |
| 5,487,378 A | * | 1/1996 | Robertson | A61M 15/0065 128/200.14 |
| 5,586,550 A | | 12/1996 | Ivri | |
| 5,707,636 A | | 1/1998 | Rodriguez | |
| 5,724,957 A | | 3/1998 | Rubsamen | |

(Continued)

FOREIGN PATENT DOCUMENTS

PL    WO 2008108672 A2 *  9/2008  ......... B05B 17/0615

OTHER PUBLICATIONS

Professional Engineering; 1999, 12(20):18-22 (only p. 18 provided).*

*Primary Examiner* — Tan-Uyen (Jackie) T Ho
*Assistant Examiner* — Joseph D Boecker
(74) *Attorney, Agent, or Firm* — Joseph F. Harding; The Small Patent Law Group, LLC (57) ABSTRACT

A nebulizer assembly configured for removable attachment to an ultrasonic actuator includes a base plate portion, a porous mesh member, and a cover member. The base plate portion includes an opening extending therethrough, and is substantially rigid such that ultrasonic vibrations from the ultrasonic actuator may be transmitted through the base plate portion to the porous mesh member to vibrate the porous mesh member. The porous mesh member is configured for passage therethrough of a nebulized fluid, and is disposed in the opening of the base plate portion proximate a fluid emission side of the nebulizer assembly. The cover member is disposed on a second side of the nebulizer assembly opposite the fluid emission side. The cover member covers the opening and defines a cavity between the cover member and the porous mesh member. The cavity is configured to retain a fluid to be nebulized.

20 Claims, 6 Drawing Sheets (56) References Cited

U.S. PATENT DOCUMENTS

| | | | |
|---|---|---|---|
| 6,196,219 B1 * | 3/2001 | Hess | A61M 15/0085 128/200.14 |
| 6,427,682 B1 | 8/2002 | Klimowicz | |
| 6,467,476 B1 | 10/2002 | Ivri et al. | |
| 6,530,370 B1 | 3/2003 | Heinonen | |
| 6,539,937 B1 | 4/2003 | Haveri | |
| 6,540,153 B1 | 4/2003 | Ivri | |
| 6,769,626 B1 | 8/2004 | Haveri | |
| 6,868,851 B2 | 3/2005 | Heinonen | |
| 6,978,779 B2 | 12/2005 | Haveri | |
| 7,472,701 B2 | 1/2009 | Pfichner | |
| 8,235,309 B2 * | 8/2012 | Xu | B64C 21/04 239/102.1 |
| 8,371,290 B2 | 2/2013 | Haveri | |
| 2002/0162551 A1 | 11/2002 | Litherland | |
| 2004/0031488 A1 | 2/2004 | Terada | |
| 2009/0134235 A1 | 5/2009 | Ivri | |
| 2009/0288659 A1 * | 11/2009 | Haveri | A61M 16/18 128/203.14 |
| 2011/0006127 A1 * | 1/2011 | Ono | A61B 17/3203 239/1 |
| 2011/0089256 A1 * | 4/2011 | Kojima | B05B 9/01 239/102.2 |
| 2012/0090710 A1 * | 4/2012 | Chen | F04B 23/04 137/565.29 |
| 2013/0327322 A1 * | 12/2013 | Bentvelsen | A61M 11/005 128/200.16 |
| 2015/0027441 A1 * | 1/2015 | Vecellio-None | A61M 11/005 128/200.16 |

* cited by examiner

```
┌─────────────────────────────────────────┐
│ Provide Housing With Ultrasonic Actuator│─602
└─────────────────────────────────────────┘
                    ↓
┌─────────────────────────────────────────┐
│  Position Nebulizer Assembly In Housing │─604
└─────────────────────────────────────────┘
                    ↓
┌─────────────────────────────────────────┐
│Contact Nebulizer Assembly With Ultrasonic Actuator│─606
└─────────────────────────────────────────┘
                    ↓
         ┌──────────────────┐
         │   Provide Fluid  │─608
         └──────────────────┘
                    ↓
         ┌──────────────────┐
         │   Disperse Fluid │─610
         └──────────────────┘
                    ↓
      ┌────────────────────────┐
      │Remove Nebulizer Assembly│─612
      └────────────────────────┘
                    ↓
      ┌────────────────────────┐
      │Dispose nebulizer assembly│─614
      └────────────────────────┘
                    ↓
┌─────────────────────────────────────────┐
│ Position Replacement Nebulizer Assembly │─616
└─────────────────────────────────────────┘
```

FIG. 6

NEBULIZER SYSTEMS AND METHODS

BACKGROUND

Nebulizers may be employed to deliver a fluid as a mist. For example, in medical applications, nebulizers may be used as drug delivery devices for delivering medication to a patient in the form of a mist that may be inhaled by the patient. As another example, water (e.g., heated water) may be delivered from a nebulizer to a patient to be inhaled for humidification. Various nebulizers may utilize oxygen, ultrasonic power (e.g., vibrations), and/or compressed air to provide droplets (e.g., aerosol droplets or mist) from solutions or suspensions. The droplets may then be inhaled, for example using a facemask operably connected to the nebulizer.

For example, certain nebulizers may employ ultrasonic vibrations to provide a mist. In some nebulizers, an electronic oscillator is used to generate a high frequency ultrasonic wave, which in turn causes a mechanical vibration of a piezoelectric element. The vibrating piezoelectric element, if in contact with a liquid (e.g., a liquid in a reservoir), may then cause a mist to be provided from the liquid. As another example, in some known nebulizers, a piezoelectric element is affixed to a mesh or membrane at an end of a liquid reservoir. Vibration of the piezoelectric element causes a vibration of the mesh or membrane and results in the passage of droplets through the mesh or membrane. Such nebulizers, however, suffer from a variety of drawbacks. For example, such nebulizers typically utilize a generally large reservoir, resulting in excessive dead volume and waste. Further, as the volume in the reservoir changes, the rate of mist production may become difficult to measure and/or control. Further still, the piezoelectric element may be affixed to the mesh or membrane, resulting in high costs of replacement (as the piezoelectric element and mesh are disposed together) and/or contamination of the piezoelectric element. Further still, such nebulizers may typically operate in only one given orientation, limiting the versatility or flexibility of use of the device.

BRIEF DESCRIPTION

In one embodiment, a nebulizer assembly (e.g., a nebulizer assembly configured for removable attachment to an ultrasonic actuator) is provided. The nebulizer assembly includes a base plate portion, a porous mesh member, and a cover member. The base plate portion includes an opening extending therethrough, and is substantially rigid such that ultrasonic vibrations from the ultrasonic actuator may be transmitted through the base plate portion to the porous mesh member to vibrate the porous mesh member. The porous mesh member is configured for passage therethrough of a nebulized fluid, and is disposed in the opening of the base plate portion proximate a fluid emission side of the nebulizer assembly. The cover member is disposed on a second side of the nebulizer assembly opposite the fluid emission side. The cover member covers the opening and defines a cavity between the cover member and the porous mesh member. The cavity is configured to retain a fluid to be nebulized.

In another embodiment, a system includes an ultrasonic actuator mounting portion, and a nebulizer assembly mounting portion. The ultrasonic actuator mounting portion is configured to secure a sonotrode in a desired position. The nebulizer assembly mounting portion is configured to releaseably accept a nebulizer assembly. The nebulizer assembly includes a base plate portion, porous mesh member, and a cover member. The base plate portion includes an opening in which the porous mesh member is disposed proximate a fluid emission side. The cover member covers the opening proximate an actuator side of the base plate portion. A cavity for retaining a fluid to be nebulized is defined between the cover member and the porous mesh member. The sonotrode, when in the desired position, contacts the nebulizer assembly when the nebulizer assembly is positioned in the nebulizer assembly mounting portion such that ultrasonic vibrations from the sonotrode are configured to pass through the base plate portion to vibrate the porous mesh member.

In another embodiment, a method is provided (e.g., a method for providing a nebulizer assembly). The method includes providing a base plate having an opening extending therethrough. The base plate includes a fluid emission side and a second side disposed opposite the fluid emission side. The method further includes securing a porous mesh member configured for ultrasonic nebulization in the opening proximate the fluid emission side. Also, the method includes securing a cover member to the base plate proximate the second side of the base plate with the cover member covering the opening and defining a cavity between the cover member and the porous mesh member. The cavity is configured to retain a fluid to be nebulized.

DETAILED DESCRIPTION

Various embodiments will be better understood when read in conjunction with the appended drawings. To the extent that the figures illustrate diagrams of the functional blocks of various embodiments, the functional blocks are not necessarily indicative of the division between componentry. Thus, for example, one or more of the functional blocks (e.g., processors, controllers or memories) may be implemented in a single piece of hardware (e.g., a general purpose signal processor or random access memory, hard disk, or the like) or multiple pieces of hardware. Similarly, any programs may be stand-alone programs, may be incorporated as subroutines in an operating system, may be functions in an installed software package, and the like. It should be understood that the various embodiments are not limited to the arrangements and instrumentality shown in the drawings.

As used herein, the terms "system," "unit," or "module" may include a hardware and/or software system that operates to perform one or more functions. For example, a module, unit, or system may include a computer processor, controller, or other logic-based device that performs operations based on instructions stored on a tangible and non-transitory computer readable storage medium, such as a computer memory. Alternatively, a module, unit, or system may include a hard-wired device that performs operations based on hard-wired logic of the device. The modules or units shown in the attached figures may represent the hardware that operates based on software or hardwired instructions, the software that directs hardware to perform the operations, or a combination thereof. As used herein, an element or step recited in the singular and proceeded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

Generally, various embodiments provide for nebulizers utilizing ultrasonic activation of a mesh or membrane to provide a mist. A nebulizer formed in accordance with various embodiments includes a base plate or portion, a mesh plate (e.g., a mesh plate with microholes passing therethrough configured for the passage of droplets or mist when the mesh plate is ultrasonically vibrated), a thin film or cover that covers all or a portion of a side of the base plate, and feed-in and feed-out tubes. The mesh plate is received in an opening of the base plate, and the thin film or cover is positioned over at least a portion of a surface of the base plate to form a cavity between the mesh plate and the thin film or cover. The feed-in and feed-out tubes are in fluid communication with the cavity.

The fluid to be atomized or nebulized may be delivered to the cavity (and to the mesh plate) using the feed-in tube. Ultrasonic energy is transmitted to the mesh plate and used to vibrate the mesh plate, causing fluid on the mesh plate to be atomized or nebulized. A constant, generally small, positive pressure may be applied to the fluid using, for example, a syringe pump to provide the fluid via the feed-in tube. Any excess fluid not emitted out of the mesh plate may be released through the feed-out tube (or a vent). The ultrasonic energy may be provided by an actuator such as a sonotrode that may be brought into or out of contact with the nebulizer assembly as desired. Because the sonotrode is not affixed to the nebulizer assembly, the nebulizer assembly may be separately disposable from the sonotrode, and the sonotrode may be reused with plural nebulizer assemblies. Further, the sonotrode may be kept out of contact with the fluid to be atomized or nebulized, thereby reducing any risk of contamination of the ultrasonic actuator.

In various embodiments, one or more different techniques may be employed to construct nebulizer assemblies. For example, one or more portions of the nebulizer assembly may be formed from a single or unitary piece (e.g., by drilling out portions, machining out portions, etching out portions, or the like). In various embodiments, laser machining and/or electrochemical machining techniques may be employed. Alternatively or additionally, various portions of a nebulizer assembly may be constructed using one or more joining processes, such as gluing, friction welding, laser welding, or the like.

In some embodiments, feed-in and feed-out tubes may be omitted, with a nebulizer assembly configured as a self-contained nebulizer assembly having a predetermined dosage of a fluid to be nebulized or atomized contained in an effectively sealed cavity. As used herein to describe an effectively sealed cavity, the term effectively sealed may be understood to mean substantially impervious to ingress or egress of a fluid for which a nebulizer was designed in the absence of ultrasonic vibration. For example, the predetermined dosage may be able to exit the cavity when the mesh plate is vibrated ultrasonically, but the predetermined dosage is maintained in the cavity when the mesh plate is not vibrated ultrasonically.

At least one technical effect of various embodiments is the provision of orientation-independent operation of a nebulizer assembly. At least one technical effect of various embodiments is improved control of nebulizer volumes and/or improved consistency of delivery of an atomized or nebulized spray or mist. At least one technical effect of various embodiments is reduced cost of nebulizer assemblies, such as disposable nebulizer assemblies that do not require an affixed ultrasonic actuator. At least one technical effect of various embodiments is improved protection against a nebulizer assembly running dry. At least one technical effect of various embodiments is the reduction or elimination of any sensors present in a flow atomization region.

Figure 1:
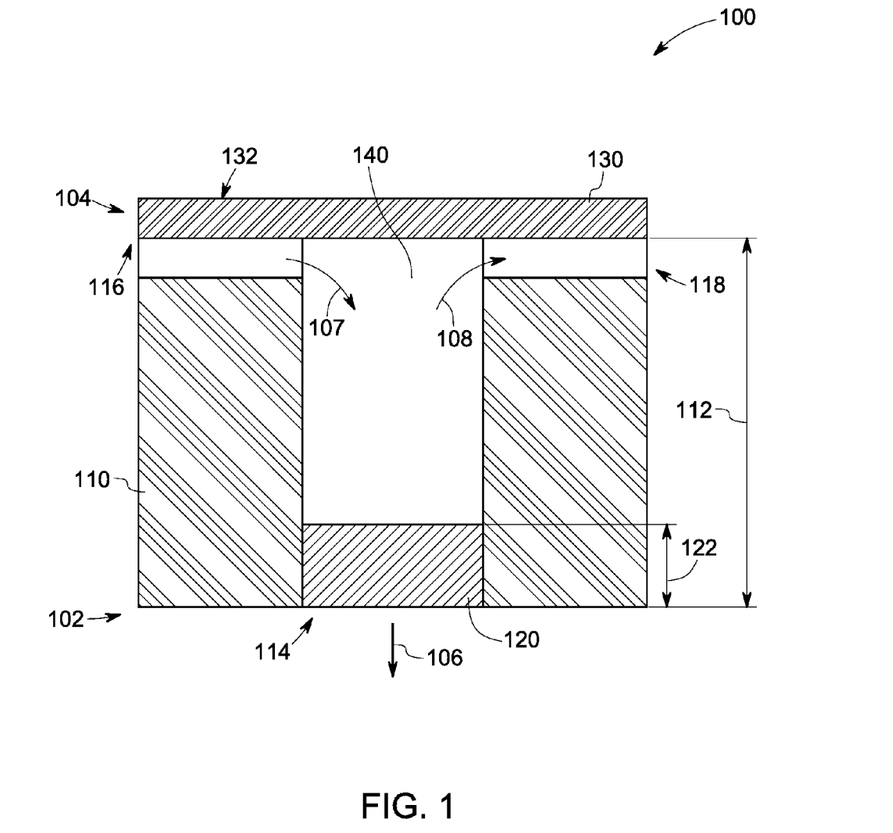
FIG. 1 is a sectional schematic diagram of a nebulizer assembly in accordance with various embodiments.

FIG. 1 is a side sectional view of a nebulizer assembly 100 formed in accordance with an embodiment. The nebulizer assembly 100 includes a base plate portion 110, a porous mesh member 120, and a cover member 130. The nebulizer assembly 100 includes a fluid emission side 102 corresponding to a direction 106 of mist or fluid flow out of the porous mesh member 120 of the nebulizer assembly 100. The nebulizer assembly 100 includes a second side 104 opposite the fluid emission side 102. In various embodiments, the second side 104 may be configured as an actuator side configured for contact with an ultrasonic actuator. With the second side 104 (or actuator side) opposite the fluid emission side 102, an actuator (e.g., a sonotrode) may be brought into contact with the second side 104 to provide ultrasonic energy to the porous mesh member 120 (e.g., via the base plate portion 110), without placing the actuator in contact with or in the path of a fluid to be atomized or nebulized. For example, the ultrasonic actuator may be placed in contact with the cover member 130 proximate the second side 104. Ultrasonic waves then pass through the cover member 130 and the base plate portion 110 to the porous mesh member 120, vibrating the porous mesh member 120 and resulting in the atomization or nebulization of fluid in contact with the porous mesh member 120, with a mist or droplets delivered in the direction 106. In various embodiments, the nebulizer assembly 100 may be operably connected with a facemask or mouthpiece such that the mist or droplets delivered in the direction 106 is directed to a patient for inhalation via the facemask or mouthpiece.

The nebulizer assembly 100 depicted in FIG. 1 includes a cavity 140 in fluid communication with a feed-in channel 116 and a feed-out channel 118. The cavity 140 may be defined, for example, between a lower surface of the cover member 130 (as shown in FIG. 1) and an upper surface of the porous mesh member 120 (as shown in FIG. 1). The cavity 140 is also in fluid communication with the porous mesh member 120. The cavity 140 is configured to retain a volume of fluid to be atomized or nebulized in contact with the porous mesh member 130. In various embodiments, the cavity 140 may be supplied with fluid from outside of the nebulizer assembly 100 along a supply path 107 via the feed-in channel 116. Additionally, fluid may be removed from the cavity 140 along a vent path 108 via the feed-out channel 118. For example, fluid may be introduced to the cavity 140 via the feed-in channel 116 under pressure along the supply path 107, for example from a syringe or pump. A first portion of the fluid may be nebulized and delivered in the direction 106 through the porous mesh member 120, while a second portion may be removed from the cavity 140 along the vent path 108 via the feed-out channel 118.

The amount of fluid nebulized may be determined (and/or controlled) using sensors detecting the flow into the feed-in channel 116 and/or out of the feed-out channel 118. Thus, in various embodiments, because sensors are disposed in one or more of a supply or return line or channel, sensors may be positioned remotely from an atomization region. Further, the pressure on the fluid in the cavity 140 may be maintained at a generally constant value by varying the supply of fluid from the feed-in channel 116 and/or the removal of fluid via the feed-out channel 118. As just one example, the fluid may be supplied at a generally constant rate, and the pressure monitored. If the pressure exceeds a predetermined threshold, a valve (not shown) associated with the feed-out channel 118 may be opened, allowing for the flow of a portion of the fluid out of the cavity via the feed-in channel 118 and reducing the pressure. Thus, in various embodiments, the volume and/or pressure of fluid in contact with the porous mesh member 120 may be maintained at a generally constant level, thereby improving consistency in the performance of the porous mesh member 120 and in the delivery of atomized or nebulized fluid and/or reducing dead volume or waste of fluid. In other embodiments, the feed-in channel 116 may be utilized to supply fluid to the cavity 140, but the feed-out channel may be omitted. For example, the pressure of fluid supplied to the cavity 140 may be monitored and controlled to be maintained generally constant.

The base plate portion 110 in the illustrated embodiment includes an opening 114. The opening 114 is sized and configured to accept and retain the porous mesh member 120 therein. The opening 114 is also configured to define sides of the cavity 140. In various embodiments, the base plate portion 110 may be configured to one or more of retain the porous mesh member 120 (e.g., provide a mounting area for the porous mesh member 120), retain fluid in the cavity 140 (e.g., by defining a portion of the cavity 140), or transmit ultrasonic waves. In various embodiments, the base plate portion 110 may be configured as having generally cylindrical, circular, or disk-shaped profile. For example, both the base plate portion 110 and the opening 114 may be substantially circular in cross-section. In other embodiments, other shapes for the opening 114 and/or base plate portion 110 may be employed.

As indicated herein, the base plate portion 110 in various embodiments is configured to be substantially rigid. As used herein, a substantially rigid base plate portion 110 may be understood as a base plate portion having sufficient rigidity to effectively transfer ultrasonic waves to the porous mesh member 120, so that the porous mesh member 120 may vibrate to disperse fluid in the cavity 140 as a mist in the direction 106. In the illustrated embodiment, the base plate portion 110 has a thickness 112 extending generally from the fluid emission side 102 to the cover member 130. For example, in various embodiments, the thickness 112 of the base plate portion 110 may be selected from a range of between about 100 to about 200 microns. In various embodiments, the base plate portion 110 may be made of, for example, stainless steel.

The nebulizer assembly 100 depicted in FIG. 1 includes a feed-in channel 116 and a feed-out channel 118. As discussed herein, the feed-in channel 116 is in fluid communication with the cavity 140 and is configured for the supply of fluid to be nebulized to the cavity 140. The feed-out channel 118 is in fluid communication with the cavity 140 and is configured for the removal of fluid from the cavity 140 (e.g., fluid that is not atomized via the porous mesh member 120. In the illustrated embodiment, the feed-in channel 116 and the feed-out channel 120 are formed utilizing etching, such as electrochemical etching. For example, open channels may be etched or otherwise formed in an upper (as seen in FIG. 1) surface of the base plate portion 110 (e.g., proximate the second side 104). The channels may be then be closed by welding, gluing, or otherwise affixing the cover member 130 to the base plate portion 110 such that the cover member 130 covers the channels, thereby providing closed channels for controlled delivery and/or removal of fluid from the cavity 140.

In alternate embodiments, for example, the channels could be machined out of an upper surface of the base plate portion 110 instead of etching. Additionally or alternatively, the channels may be formed entirely or partially by machining, etching, or otherwise removing a portion of a bottom (as seen in FIG. 1) surface of the cover member 130. In still other embodiments, the base plate portion 110 and cover member 130 may be formed initially as a unit, with the cavity 140 formed by boring to a predetermined depth from the fluid emission side 102, and the feed-in channel 116 and the feed-out channel 118 formed by drilling from the sides of the base plate portion 110 and/or cover member 130 to meet the cavity 140. In still other embodiments, the feed-in channel 116 and/or the feed-out channel 118 may be formed using a tube or the like. It may be noted that in various embodiments, plural feed-in channels and/or plural feed-out channels may be employed. It may also be noted that, in some embodiments, the feed-out channel 118 may be omitted, while in still other embodiments, both the feed-in channel 116 and the feed-out channel 118 may be omitted (e.g., in embodiments where the nebulizer assembly 100 is formed including a predetermined dosage).

The porous mesh member 120 is disposed within the opening 112 of the base plate portion 110 and in fluid communication with the cavity 140. For example, the porous mesh member 120 may be made of, for example, stainless steel, and may be welded in position in the opening 114 of the base plate portion 110. In various embodiments, alternate compositions and/or alternate fabricating techniques may be employed. In the illustrated embodiment, the porous mesh member 120 is positioned substantially flush with a bottom surface (as seen in FIG. 1) of the base plate portion 110 proximate the fluid emission side 102.

The porous mesh member 120 is configured to provide an atomized or nebulized mist in the direction 106 from a fluid in the cavity 140 when the porous mesh member 120 is subject to ultrasonic vibration. For example, the porous mesh member 120 may include generally small holes (e.g., microholes) passing therethrough generally parallel to the direction 106. The particular size and arrangement of the holes may be selected based upon, for example, the fluid to be atomized or nebulized, the type of material and/or thickness of the porous mesh member 120, the amplitude and/or frequency of the ultrasonic vibration to be applied, or the like. Generally, the holes are small enough to impede passage therethrough of the fluid to be atomized when no ultrasonic vibration is applied to the porous mesh member 120, but large enough to allow passage of droplets of the fluid (e.g., droplets that from a mist) when ultrasonic energy is applied to the porous mesh member 120. In some embodiments, the ultrasonic energy may be applied directly to the porous mesh member. In contrast, in the illustrated embodiment, ultrasonic energy may be applied indirectly to the porous member. For example, ultrasonic energy may be applied to the either the cover member 130 and/or the base plate portion 110 proximate the second side 104 and transmitted through the base plate portion 110 to the porous mesh member 120.

In the illustrated embodiment, the porous mesh member 120 has a thickness 122. For example, in various embodiments, the thickness 122 may be about 20 microns. The thickness in various embodiments may be selected based upon the amount and/or type of fluid to be atomized, the material used for the porous mesh member 120, the amount of ultrasonic energy to be applied to the porous mesh member 120, or the like. In the illustrated embodiments, the porous mesh member 120 is depicted positioned in the opening 114 such that a bottom surface (as seen in FIG. 1) of the porous mesh member 120 is substantially flush with a bottom surface (as seen in FIG. 1) of the base plate portion 110 proximate the fluid emission side 102.

The cover member 130 of the illustrated embodiment is positioned above (as seen in FIG. 1) the base plate portion 110 proximate the second side 104. Generally, in the illustrated embodiment, the cover member 130 is configured to provide a surface defining a boundary for one or more fluid containment portions or volumes, such as the cavity 140, the feed-in channel 116, and/or the feed-out channel 118. In various embodiments, the cover member 130 may be configured to substantially cover an entire upper surface of the base plate portion 110, while, in other embodiments, the cover member 130 may be configured to cover only a portion of an upper surface of the base plate portion 110 (e.g., a portion corresponding to fluid containment volumes or portions). In the illustrated embodiment, the cover member 130 is configured as a thin film of stainless steel (e.g., the same material as the base plate portion) friction welded to an upper (as seen in FIG. 1) surface of the base plate portion 110. Other materials and/or configurations for the cover member 130 may be employed in alternate embodiments. In the illustrated embodiment, the cover member 130 and the base plate portion 110 are joined to form a substantially rigid piece that is configured to transfer ultrasonic energy applied to the second side 104 of the nebulizer assembly 100 to the porous mesh member 120 to vibrate the porous mesh member 120 for atomization of a fluid contained in the cavity 140. For example, the upper surface of the cover member 130 as seen in FIG. 1 is configured as an actuator contact surface 132 configured for contact with an ultrasonic actuator. Ultrasonic energy may be applied to the actuator contact surface 132, transmitted through the cover member 130 to the base plate portion 110, and then transmitted through the base plate portion 110 to the porous mesh member 120.

As seen in FIG. 1, the cavity 140 of the illustrated embodiment has a volume defined laterally by the sides or walls of the opening 114 of the base plate portion 110, bounded on the top by the cover member 130, and bounded on the bottom by the porous mesh member 120. Thus, for example, in the illustrated embodiment, if the thickness 112 of the base plate portion 110 is between about 100 and 200 microns, and the thickness of the porous mesh member 120 is about 20 microns, then the height of the cavity 140 is between about 80 to 180 microns. Other sizes of cavities may be employed in various embodiments. Generally the height and/or lateral dimensions of the cavity 140 may be configured or selected based on the type of fluid to be atomized, the delivery rate of fluid to be atomized, the configuration of the porous mesh member 120, the total amount of fluid to be provided as an atomized or nebulized mist (e.g., in embodiments where the cavity is effectively sealed and includes a predetermined dose), or the like. In various embodiments, the cavity 140 (and/or other aspects or portions of the nebulizer assembly 100) may be sized or configured to reduce or minimize the volume of the cavity 140 within acceptable performance parameters. Thus, the amount of dead volume may be reduced or minimized.

In various embodiments, the fluid to be atomized may be maintained at a constant volume and/or pressure in the cavity 140 via control of the flow through the feed-in channel 116 and/or through the feed-out channel 118. In some embodiments, the cavity 140 may be substantially entirely filled with a fluid for atomization, while in other embodiments the cavity 140 may include a first volume of atomization fluid and a second volume of gas (e.g., air). Maintaining the operating conditions of the fluid in the cavity 140 (e.g., the pressure and/or volume of fluid in the cavity 140) in various embodiments may provide improved consistency in the delivery of mist in the direction 106. In contrast, for example, conventional gravity driven nebulizers may experience considerable reductions or changes in delivery rate as the volume of a fluid to be atomized (and resulting pressure) in a reservoir deplete. Further, by controlling the flow through the feed-in channel 116, for example, a pressure may be maintained on the fluid in the cavity 140 such that the direction 106 may be oriented in virtually any direction. Further still, the amount of fluid being delivered in the direction 106 from the nebulizer assembly may be determined using information detected in one or more of a supply line to the nebulizer assembly 100 or an exit line from the nebulizer assembly 100, allowing for remote determination of fluid delivered and eliminating or reducing the need for sensor or detectors disposed proximate the atomization region.

Figure 2:
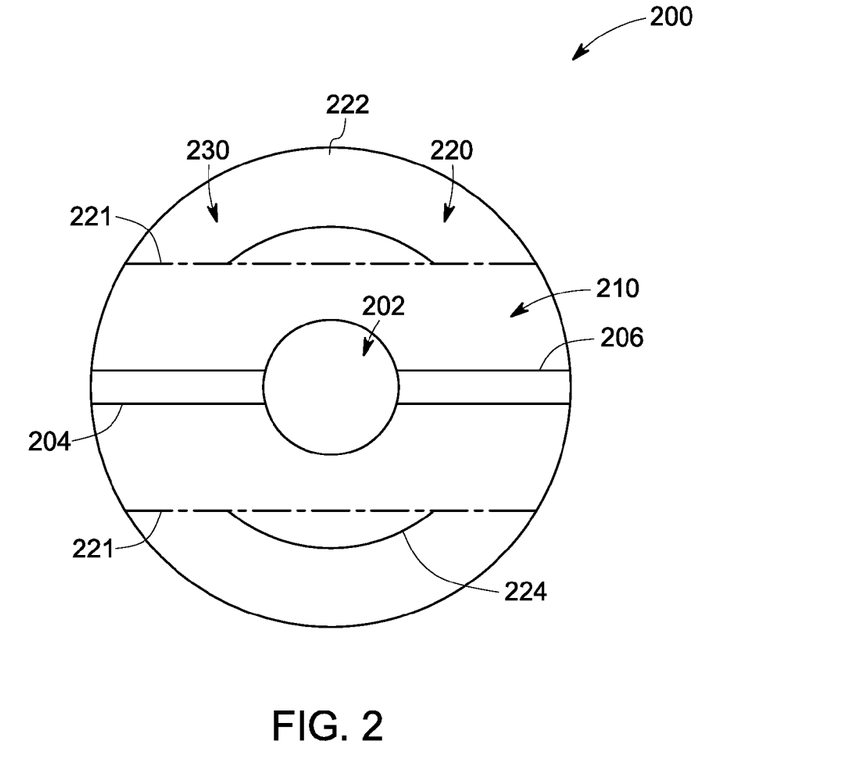
FIG. 2 is a top view of a nebulizer assembly in accordance with various embodiments.

FIG. 2 is a top view of an actuator contact side 230 of a nebulizer base plate portion 200 in accordance with one embodiment. As indicated herein, in some embodiments, a cover member may cover only a given portion of a base plate portion, for example a portion including any fluid containment areas. In FIG. 2, an outline of the placement of a corresponding cover member is depicted by phantom lines 221. Thus, a covered portion 210 is defined inside of the phantom lines 221 and an exposed portion 220 is defined outside of the phantom lines 221. The nebulizer base plate 200 includes an opening 202 extending therethrough, a feed-in channel 204 formed into the actuator contact side 230, and a feed-out channel 206 formed into the actuator contact side 230. The opening 202 in the illustrated embodiment is configured to accept a porous mesh member (not shown in FIG. 2; see, e.g., porous mesh member 120 of FIG. 1). When the cover member and porous mesh member are joined to the base plate portion 200, the opening 202 may define the lateral bounds of a cavity configured to maintain fluid in contact with the porous mesh member. As seen in FIG. 2, the covered portion 210 configured for placement of the cover member includes the portions of the base plate portion 200 configured for fluid containment (e.g., the opening 202, feed-in channel 204, and feed-out channel 206) within the bounds of the covered portion 210. In FIG. 2, one feed-in channel 204 and one feed-out channel 206 are depicted substantially aligned with each other (e.g., a path through the channels defines a substantially straight line).

However, in alternate embodiments, more than one of either (or both) types of channels may be employed, and/or the channels may not be substantially aligned with each other.

In the embodiment depicted in FIG. 2, the exposed portion 220 is configured for contact with an ultrasonic actuator that may be brought into and out of contact with the base plate portion 200. Thus, the ultrasonic actuator may be understood as functionally removable from the nebulizer assembly. A functionally removable component as used herein may be understood as a component that may be brought into and out of contact with another component without damaging or altering the functional capability of either component. For clarity and avoidance of doubt, a piezoelectric element affixed directly to a conventional mesh membrane may not be understood as functionally removable because destructive means may be required to remove the piezoelectric element and/or the conventional mesh membrane may not be capable for the intended function of the membrane without the piezoelectric element permanently affixed.

In the illustrated portion, the exposed portion 220 of the actuator contact side 230 of the base plate portion 200 includes a contact surface 222 configured for contact with an ultrasonic actuator. For example, a sonotrode may be brought into contact with the contact surface of 222 for delivery of ultrasonic energy. After nebulization is complete, the sonotrode may be readily withdrawn from the contact surface 222 of the base plate portion 200 without damage or structural alteration to either. Thus, either or both of the sonotrode and nebulizer assembly may be used interchangeably with other nebulizer assemblies or sonotrodes, respectively.

To assist in the placement of the ultrasonic actuator, the contact surface 222 of the illustrated embodiment includes a contact mark 224. In the illustrated embodiment, the contact mark 224 is configured as plural arcs about a center of the base plate portion 200 corresponding to a nodal point or harmonic node of the nebulizer assembly. The location of the harmonic node and corresponding contact mark 224 may be defined by or determined based on the geometry of the nebulizer assembly. For example, for a generally (or cylindrical) cross-section, the harmonic node may be located at one or more proportions of the radius of the generally circular cross-section (e.g., r/2, r/3, or the like). The harmonic node may be located otherwise for different geometries. Thus, for a given nebulizer assembly geometry, the harmonic node may be determined experimentally and/or empirically, and a corresponding mark (or marks) placed on a contact surface for convenient and accurate placement of an ultrasonic actuator.

Figure 3A:
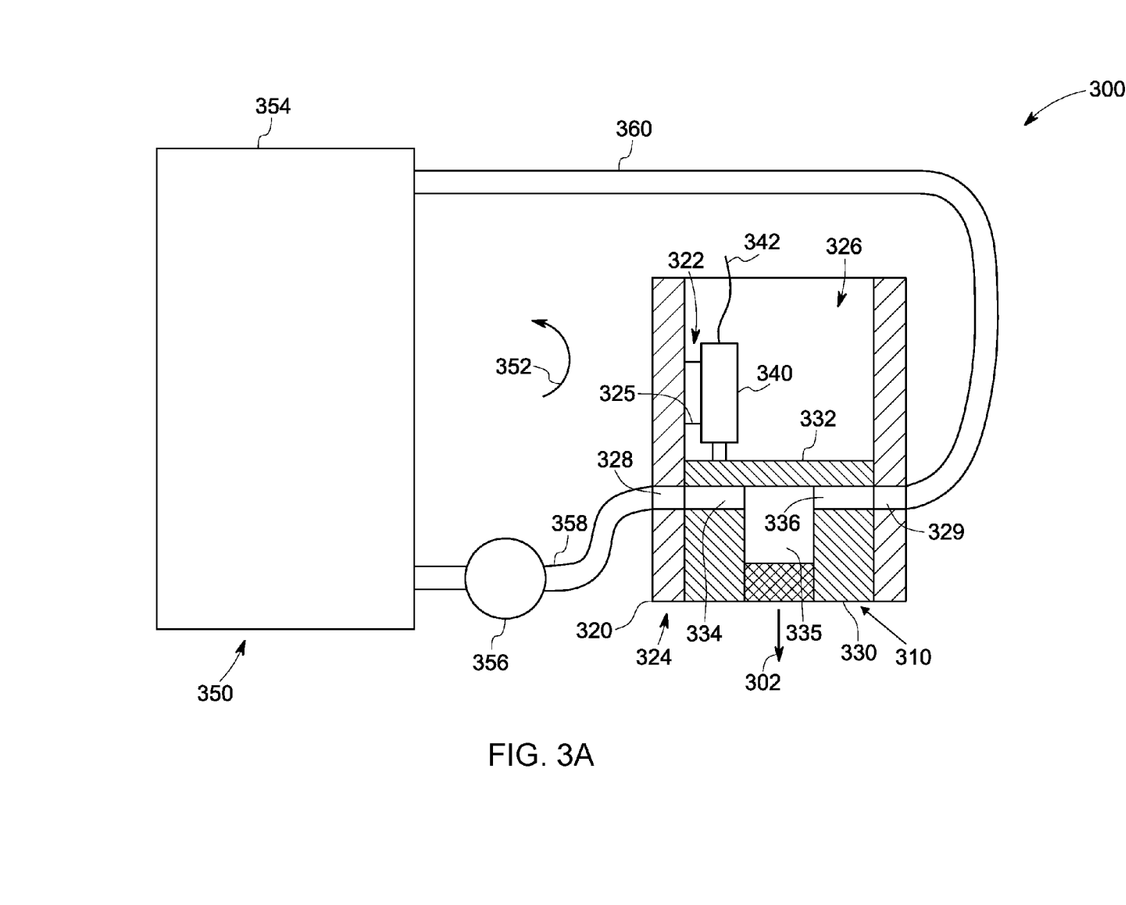
FIG. 3A is a schematic view of a nebulizer delivery system in accordance with various embodiments.

FIG. 3A is a schematic view of a nebulizer delivery system 300 formed in accordance with an embodiment. In the illustrated embodiment, the nebulizer delivery system 300 includes a nebulizer assembly 310, a housing 320, an ultrasonic actuator 340, and a fluid supply module 350. Generally, in various embodiments, the fluid supply module 350 is configured to provide a fluid to be atomized to the nebulizer assembly 310, which emits the fluid as a mist in the direction 302. For example, the fluid to be atomized may be an anesthetic agent circulated between a reservoir of the fluid supply module 350 and the nebulizer assembly 310. The amount of fluid supplied by the fluid supply module 350 to the nebulizer assembly 310 and the amount of fluid returned to the fluid supply module 350 from the nebulizer 310 may be used to determine the amount of fluid delivered as an atomized or nebulized mist. In various embodiments, the fluid supply module 350 may be configured to provide fluid to be nebulized under pressure, such that the direction 302 of fluid or mist emission may be oriented as desired, and may be oriented independently of gravitational forces.

The housing 320 is configured to accept and/or maintain the ultrasonic actuator 340 and the nebulizer assembly 310 in position for delivery of a mist. In the illustrated embodiment, the ultrasonic actuator 340 is contacted to an exterior surface of the nebulizer assembly 310 and configured to provide ultrasonic energy or waves that are transmitted through the nebulizer assembly 310 to a porous mesh member, causing the porous mesh member to vibrate and facilitating the passage of droplets through the vibrating porous mesh member. In various embodiments, the housing 320 may include clips, latches, detents, or the like to releasably accept the nebulizer assembly 310. The nebulizer assembly 310 may be configured, for example, as a disk or cartridge that may be inserted into a slot of the housing 320 and retained in a desired position. The nebulizer assembly 310 may be understood as releasably accepted by the housing 320 in that the nebulizer assembly 310 may be readily inserted and removed without damage or breakage to the housing 320, the nebulizer assembly 310, or the ultrasonic actuator 340. For example, the ultrasonic actuator 340 and the nebulizer assembly 310 may be brought into contact with each other, but not affixed or adhered to each other, so that the ultrasonic actuator 340 and the nebulizer assembly 310 may be readily separated from each other. The nebulizer assembly 310 and the housing 320 may be designed or configured for ease of removal and insertion of the nebulizer assembly 310 into the housing 320, and, in various embodiments, plural nebulizer assemblies may be sequentially removed from and added to the housing 320, with nebulizer assemblies being separately disposable from the housing 320 and the ultrasonic actuator 340 after usage of a particular individual nebulizer assembly 310. In various embodiments, including the embodiment depicted in FIG. 3A, the nebulizer assembly 310 may be configured to receive fluid from the fluid supply 350. It should be noted that, in alternate embodiments, the nebulizer assembly 310 may be a self-contained unit having a pre-loaded dosage of fluid before insertion into the housing 320.

In the illustrated embodiment, the nebulizer assembly 310 is configured to be releasably mountable in the housing 320, to receive a fluid to be atomized from the fluid supply module 350, and to deliver a mist in the direction 302. In the illustrated embodiment, the nebulizer assembly 310 delivers a mist under the influence of ultrasonic energy provided by the ultrasonic actuator 340. The nebulizer assembly 310 may be generally similar in certain respects to the nebulizer assembly 100 discussed in connection with FIG. 1.

The nebulizer assembly 310 includes an emission side 330 and an actuator contact surface 332. The nebulizer assembly 310 is configured to emit a mist in the direction 302 from the emission side 330 (e.g., via a vibrating porous mesh member). The actuator contact surface 332 is configured to provide a location for contact with the ultrasonic actuator 340. In the illustrated embodiment, the actuator contact surface 332 is disposed opposite the emission side 330 of the nebulizer assembly 310, such that the ultrasonic actuator 340 is not in a fluid emission path from the nebulizer assembly 310.

The nebulizer assembly 310 depicted in FIG. 3A includes a cavity 335, a feed-in channel 334, and a feed-out channel 336. The cavity 335 is configured to maintain a volume of a fluid to be atomized proximate to a porous mesh member of the nebulizer assembly 310. The cavity 335 in the illustrated embodiment is configured to receive fluid from the fluid supply module 350 via the feed-in channel 334 and to return fluid to the fluid supply module 350 via the feed-out channel 336.

As indicated herein, in the illustrated embodiment, the housing 320 is configured to accept and/or maintain the ultrasonic actuator 340 and the nebulizer assembly 310 in position for delivery of a mist. In some embodiments the housing 320 may be configured to be fixed (e.g., mounted to a table, wall, support, or other structure) while, in some embodiments, the housing 320 may be configured to be handheld. The housing 320 may be configured in various embodiments for attachment to a mask or mouthpiece (not shown) for delivery of an atomized mist to a patient. In the depicted embodiment, the housing 320 includes an opening 326, an actuator mounting portion 322 and a nebulizer assembly mounting portion 324. The opening 326 is configured for insertion and/or removal of the ultrasonic actuator 340 and/or the nebulizer assembly 310 into the housing 320.

Figure 3B:
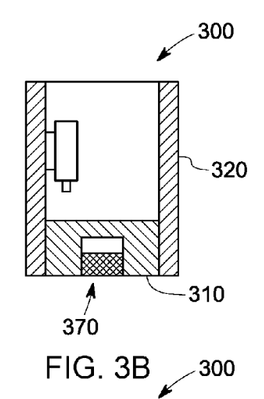
FIG. 3B is an enlarged view of a portion of the nebulizer delivery system of FIG. 3A, in accordance with various embodiments.

The actuator mounting portion 322 is configured to secure or retain the ultrasonic actuator 340 in the housing 320 in one or more desired positions relative to the nebulizer assembly 310. For example, the actuator mounting portion 322 may include one or more posts 325 configured to maintain the ultrasonic actuator 340 in a position corresponding to contact with a harmonic node of the nebulizer assembly 310. The actuator mounting portion 322 may allow for adjustable mounting of the ultrasonic actuator 340 to allow for fine-tuning of the positioning of the ultrasonic actuator relative to the harmonic node of the nebulizer assembly 310. The actuator mounting portion 322 may include one or more of posts, tracks, rails, latches, fasteners, detents, or the like.

The housing 320 (e.g., the actuator mounting portion 322 of the housing) may be configured to allow movement of the ultrasonic actuator 340 between a disengaged position 370 (see FIG. 3B) and an engaged position 380 (see FIG. 3C). For example, the ultrasonic actuator 340 may be mounted on a track, rail, or the like configured for linear actuation of the ultrasonic actuator 340 between the disengaged position 370 and the engaged position 380. Further, the housing 320 may be configured to releasably lock or secure the ultrasonic actuator 340 in the disengaged position 370 and/or the engaged position 380. For example, the ultrasonic actuator 340 may be placed in the disengaged position 370 for insertion of the nebulizer assembly 310 into the housing 320 (or removal of the nebulizer assembly 310 from the housing 320). With the nebulizer assembly 310 in position as desired, the ultrasonic actuator 340 may be translated in the engagement direction 382 to be brought into contact with an exterior surface of the nebulizer assembly 310 (e.g., actuator contact surface 332) in the engaged position 380 to deliver ultrasonic energy to the nebulizer assembly 310. Before removal of the nebulizer assembly 310 from the housing 320, the ultrasonic actuator 340 may be translated in the disengagement direction 384 to the disengaged position 370.

The nebulizer assembly mounting portion 324 in the illustrated embodiment is configured to accept and secure the nebulizer assembly 310 in a desired position. For example, in the illustrated embodiment, the nebulizer assembly 310 may be inserted into the bottom (as seen in FIG. 3A) of the opening 326 of the housing 320 and snappably, latchably, or otherwise retained in position. In alternate embodiments, the nebulizer assembly 310 may be inserted via one or more slots, inserted from the top of the opening 326, secured to an external or exterior portion of the housing 320, or the like. The nebulizer assembly mounting portion 324 may include one or more of latches, clips, fasteners, guides, detents, or the like to releasably accept the nebulizer assembly 310. The nebulizer assembly mounting portion 324 and the nebulizer assembly 310 may include cooperating or corresponding guides or other features configured to provide a desired alignment of the nebulizer assembly 310 in the housing 320. For example, the nebulizer assembly mounting portion 324 may be configured to accept the nebulizer assembly 310 in a position or orientation in which a supply hole 328 aligns with the feed-in channel 334 for supply of fluid to the cavity 335, and in which an exit hole 329 aligns with the feed-out channel 336. The supply hole 328 and the exit hole 329 may be configured to accept a hose or tube of the fluid supply module 350 for transfer of fluid between the nebulizer assembly 310 and the fluid supply module 350.

The ultrasonic actuator 340 is configured to provide ultrasonic energy or waves to the nebulizer assembly 340. In the illustrated embodiment, the ultrasonic actuator 340 is positioned in the housing 320 such that, when in the engaged position 380, the ultrasonic actuator 340 contacts the actuator contact surface 332 of the nebulizer assembly 310. The ultrasonic actuator 340 in various embodiments includes a power supply 342. In the illustrated embodiment, the ultrasonic actuator 340 is shown with a power supply 342 configured as a cord for connection with an external source, such as an AC outlet. In various embodiments, the power supply 342 may be configured otherwise. For example, an internal battery disposed within the ultrasonic actuator 340 may be employed, or, as another example, a battery external to the ultrasonic actuator may be located, for example, in the opening 326. In various embodiments, the ultrasonic actuator 340 may be a sonotrode, for example generally similar to devices utilized for ultrasonic welding.

The fluid supply module 350 is configured to provide fluid to be atomized to the nebulizer assembly 310. In the illustrated embodiment, the fluid supply module 350 defines circuit 352 including a reservoir 354, a supply line 358, a return line 360, and a pressure delivery module 356. Generally the circuit 352 is configured to provide fluid from the reservoir 354 to the cavity 335 for atomization, and to return an amount of fluid returned from the cavity 335. Thus, some fluid may exit the cavity 335 as a mist in the direction 302 while other fluid may exit the cavity 335 via the return line 360 (e.g., from the cavity 335, through the feed-out channel 336, and through the return line 360 to the reservoir 354).

The reservoir 354 is configured to retain a desired amount of fluid. For example, the reservoir 354 may retain an amount of fluid (e.g., an anesthetic agent) that is substantially larger than an amount retained in the cavity 335. For example, the reservoir 354 may be permanently or releasably coupled with plural nebulizer assemblies and be configured to provide fluid to the plural nebulizer assemblies. The supply line 358 is configured to provide a fluid path from the reservoir 354 to the cavity 335. For example, the supply line 358 may operably connect to the feed-in channel 334. In various embodiments, the supply line 358 may include one or more of tubing, piping, hosing, or the like, and may also include fittings, clamps, valves, nozzles, or the like for connection to other components and/or control of flow through the supply line 358. The return line 360 is configured to provide a fluid path to the reservoir 354 from the cavity 335. For example, the return line 360 may operably connect to the feed-out channel 336. In various embodiments, the return line 360 may include one or more of tubing, piping, hosing, or the like, and may also include fittings, clamps, valves, nozzles, or the like for connection to other components and/or control of flow through the return line 360.

Figure 3C:
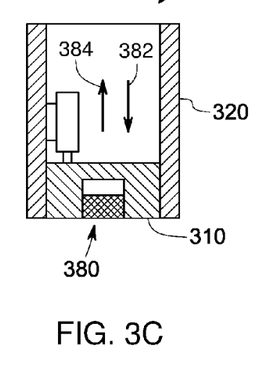
FIG. 3C is an enlarged view of a portion of the nebulizer delivery system of FIG. 3A, in accordance with various embodiments.

In the illustrated embodiment, the pressure delivery module 356 is shown as a single unit disposed along the supply line 358. In other embodiments, the pressure delivery module 356 may be disposed along the return line 360. In alternate embodiments, the pressure delivery module 356 may be comprised of multiple units disposed at various points throughout the circuit 352. For example, the pressure delivery module 356 may include a pump located along the supply line, a sensor located along the supply line, and a sensor located along the return line, along with a controller. One or more settings of the pump and/or valves positioned along the circuit 352 may be controlled by the controller to provide a desired rate of fluid delivery to the cavity 335 and/or to maintain a desired pressure in the cavity 335. For example, the rate of mist delivery may be determined using information from a flow sensor disposed along the supply line and information from a flow sensor disposed along the return line. The controller may adjust the flow of fluid (e.g., by increasing the effort from the pump and/or adjusting settings of one or more valves in the supply line 358 and/or the return line 360) to or from the cavity 335 responsive to the determined rate of mist delivery (e.g., increasing flow to the cavity 335 if the rate is below a desired threshold or outside of a desired range).

In the illustrated embodiment, the pressure delivery module 356 is configured to provide a pressure for delivery of fluid to the cavity 335. The pressure delivery module 356 may include a pump, such as a syringe pump, peristaltic pump, vacuum pump, or the like. The pressure delivery module 356 may also be configured to maintain a desired pressure in the circuit 352 and/or in the cavity 335. For example, the pressure delivery module 356 may include a controller and one or more sensors or detectors, with the controller configured to increase or decrease a pressure provided by the pump responsive to pressure information from the sensors. Thus, in various embodiments, a rate of fluid delivery may be effectively monitored or controlled, and/or a pressure (and/or volume) of fluid in the cavity 335 may be maintained at a generally constant value for consistent, reliable performance of the nebulizer assembly 310. In various embodiments, sensors may thus be placed remotely from the atomization region (e.g., along a supply and/or return line), and delivery rates may be reliably measured and controlled.

Figure 4:
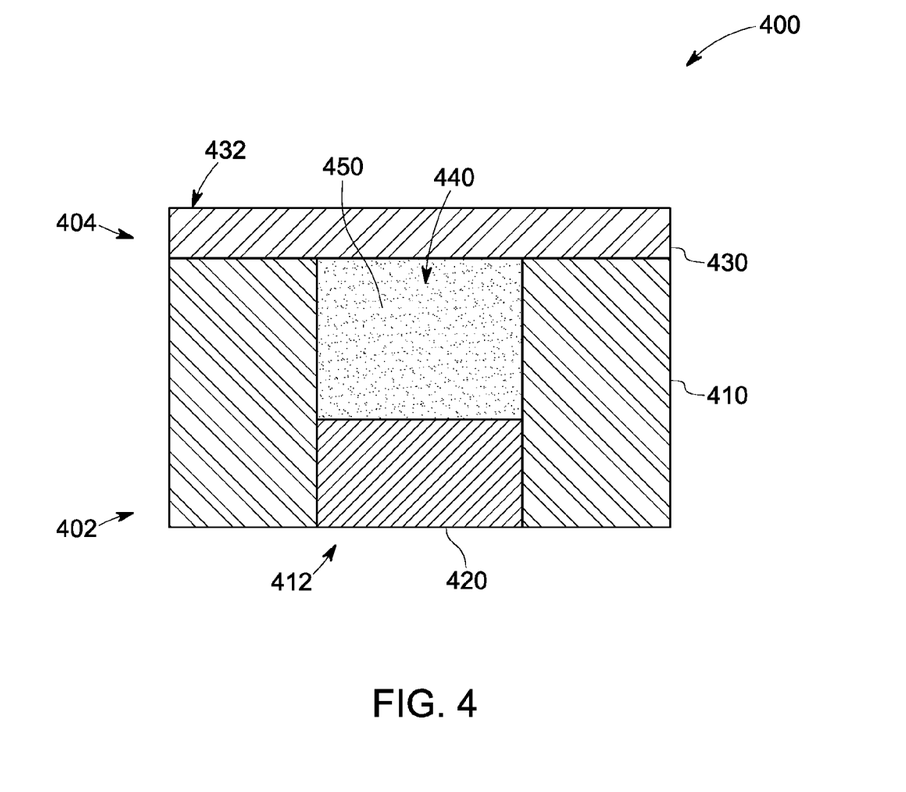
FIG. 4 is a schematic view of a self-contained nebulizer assembly in accordance with various embodiments.

FIG. 4 provides a side sectional view of a self-contained nebulizer assembly 400. The nebulizer assembly 400 may contained a predetermined dosage of medicine to be atomized. In various embodiments, the nebulizer assembly 400 may be configured as a single use nebulizer intended to be used one time and then disposed. Because the nebulizer assembly 400 is devoid of sensors or piezoelectric devices, disposal of the nebulizer assembly 400 may be more cost efficient than disposal of nebulizer devices that have sensors, piezoelectric devices, or the alike affixed thereto. The nebulizer assembly 400 may be provided in a blister-pack configuration. In the illustrated embodiment, the nebulizer assembly 400 includes a cavity 440 including a predetermined dosage of medicine 450. In various embodiments, the nebulizer assembly 400 may be configured for ready insertion and/or removal from a housing (e.g., housing 320).

As seen in FIG. 4, the nebulizer assembly 400 may be generally similar in certain respects as the nebulizer assembly 100 discussed herein in connection with FIG. 1. The nebulizer assembly 400 includes a base plate portion 410, a porous mesh member 420, and a cover member 432. As the depicted nebulizer assembly 400 is configured to be self-contained and not to receive fluid from (or return fluid to) an external reservoir, the nebulizer assembly 400 in the depicted embodiment does not include a feed-in or a feed-out channel. The nebulizer assembly 400 includes a fluid emission side 402 (from which side a mist is emitted from the porous mesh member 420) and a second side 404 (or actuator side). The cover member 430 includes a surface 432 proximate the second side 404 configured for contact with an ultrasonic actuator (not shown in FIG. 4), whereby ultrasonic energy from the ultrasonic actuator may be transferred through the base plate portion 410 to the porous mesh member 420, causing the porous mesh member 420 to vibrate and disperse a fluid to be atomized (e.g., fluid from the predetermined dosage of medicine 450) and dispersed from the fluid emission side 402 of the nebulizer assembly 400. The base plate portion 410 includes an opening 412 configured to accept the porous mesh plate 420 proximate the fluid emission side 402. The cavity 440 is defined in the opening 412 between the porous mesh plate 420 and the cover member 430. The cover member 430 is configured to cover at least the opening 412 proximate the second side 404, such that the cavity 440 is configured as an effectively sealed cavity effectively sealed.

In the illustrated embodiment, the predetermined dosage of medicine 450 is provided in the cavity 440 before the cavity is effectively sealed (e.g., before the securement of the porous mesh member 420 in the opening 412 or the joining of the cover member 430 to the base plate portion 410). Thus, the predetermined dosage of medicine 450 may be retained in the cavity 440 of the nebulizer assembly 400 until an appropriate vibration of the porous mesh plate 420 is initiated, at which point fluid from the predetermined dosage of medicine 450 may be atomized and dispersed out of the fluid emission side 402 of the nebulizer assembly 400. Thus, in various embodiments, a cost effective, easily disposable nebulizer assembly having a regulated or predetermined dosage of medicine may be provided. Further, in various embodiments, plural nebulizer assemblies (e.g., of the same dosage, of different dosages, of different medicines) may be used interchangeably with an ultrasonic actuator, allowing for re-use of the ultrasonic actuator with different nebulizer assemblies and/or fluids to be atomized.

Figure 5:
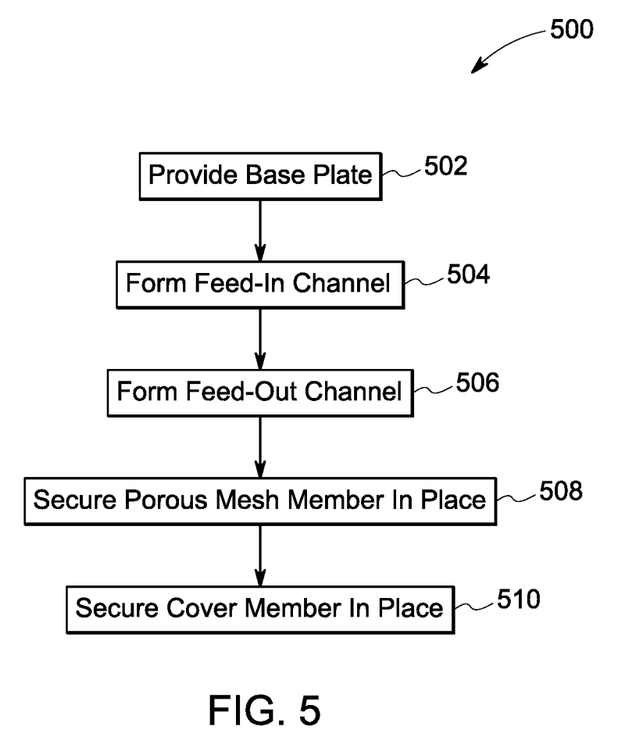
FIG. 5 is a flowchart of a method for providing a nebulizer assembly in accordance with various embodiments.

FIG. 5 is a flowchart for a method 500 (e.g., a method for providing a nebulizer assembly) in accordance with an embodiment. In various embodiments, the method 500, for example, may employ structures or aspects of various embodiments (e.g., systems and/or methods) discussed herein. In various embodiments, certain steps may be omitted or added, certain steps may be combined, certain steps may be performed simultaneously, certain steps may be performed concurrently, certain steps may be split into multiple steps, certain steps may be performed in a different order, or certain steps or series of steps may be re-performed in an iterative fashion.

At 502, a base plate is provided. The base plate, for example, may be configured substantially similarly in respects to the base plate portion 110 discussed herein in connection with FIG. 1. The base plate, for example, may include an opening extending therethrough configured to accept a porous mesh member. The base plate may be configured to be substantially rigid, so that the base plate may transfer ultrasonic waves or energy to the porous mesh member when the porous mesh member is disposed in the opening of the base plate. The base plate, for example, may be constructed of stainless steel.

At 504, a feed-in channel is formed. The feed-in channel may be formed in a surface of the base plate and may extend from an exterior perimeter of the base plate to the opening of the base plate, thereby providing a path of fluid communication between the opening and the exterior of the base plate for the introduction of a fluid to be atomized or nebulized. The depth of the feed-in channel may be selected to provide a desired amount of fluid to the porous mesh member during atomization. For example, the depth of the feed-in channel may be selected to match or exceed a desired rate of delivery of atomized or nebulized fluid. The feed-in channel may be formed by an etching process (e.g., electrochemical etching), or as another example, by machining (e.g., laser machining). In alternate embodiments, the feed-in channel may be formed entirely or partially by etching or machining into a cover member to be affixed to the base plate. In still other embodiments, an already formed conduit such as a tube or hose may be used to form the feed-in channel and may, for example, be placed in a slot or otherwise interposed between the base plate and the cover member. As yet one more example, the feed-in channel may be formed by drilling through the base plate. As still one more example, the feed-in channel may be formed as part of a casting process for providing the base plate and/or the cover member.

At 506, a feed-out channel is formed. The feed-out channel may be formed in a surface of the base plate and may extend from an exterior perimeter of the base plate to the opening of the base plate, thereby providing a path of fluid communication between the opening and the exterior of the base plate for the release or removal of a fluid used for atomization or nebulization. For example, a supply of fluid to be nebulized may be provided via the feed-in channel formed at 504. A portion of the fluid supplied via the feed-in channel may be atomized. However, for example, to maintain a desired pressure in a cavity associated with a porous mesh member, an amount of fluid may not be atomized, but instead vented from the cavity via the feed-out channel. The depth of the feed-out channel may be selected to provide a desired venting or pressure release capability during atomization. In some embodiments, the depth of the feed-out channel may be selected to match the depth of the feed-in channel. For example, the feed-in channel and feed-out channel may be formed as part of a single or shared etching or machining process. The feed-out channel may be formed by an etching process (e.g., electrochemical etching), or as another example, by machining (e.g., laser machining). In alternate embodiments, the feed-out channel may be formed entirely or partially by etching or machining into a cover member to be affixed to the base plate. In still other embodiments, an already formed conduit such as a tube or hose may be used to form the feed-out channel and may, for example, be placed in a slot or otherwise interposed between the base plate and the cover member. As yet one more example, the feed-out channel may be formed by drilling through the base plate. As still one more example, the feed-out channel may be formed as part of a casting process for providing the base plate and/or the cover member.

At 508, a porous mesh member is secured in place. The porous mesh member in various embodiments is mounted or fixed in the opening of the base plate and positioned proximate a fluid emission side so that a mist may exit the nebulizer assembly from the porous mesh member in a desired direction. The porous mesh member may be secured in place, for example, by welding, or, as another example, by gluing. The porous mesh member may be joined to the base plate in a secure or rigid fashion such that ultrasonic energy or waves may be transmitted through the base plate to the porous mesh member. Further, the porous mesh member is sized and configured to vibrate when provided with ultrasonic energy or waves via the base plate. The vibration is used to emit fluid through microholes of the porous mesh member otherwise small enough to retain the fluid in the cavity (e.g., when not under the influence of ultrasonic energy or waves sufficient to cause a given amount of vibration).

At 510, a cover member is secured in place. In various embodiments, the cover member may be formed as a generally thin foil of stainless steel, for example made of stainless steel. The cover member may be secured in place to a side of the base plate opposite the fluid emission side, and may be secured in place by welding, gluing, or the like. The cover member in various embodiments is configured to cover at least a portion of a surface of the base plate corresponding to fluid containment areas (e.g., the opening in which the porous mesh member was secured at 508, the feed-in channel formed at 504, the feed-out channel formed at 506). In some embodiments, the cover member may cover substantially an entire surface of the base plate, while in other embodiments the cover member may not cover substantially the entire surface. Thus, the cover member may serve as a boundary for or help define one or more fluid containment areas. For example, when the cover member covers the opening in which the porous mesh member has been secured, a cavity is defined in the opening between the cover member and the porous mesh member. The cavity provides a volume for fluid containment for the fluid to be atomized via the porous mesh member. Other methods for forming the cover member, base plate, and/or other aspects of the nebulizer assembly may be employed in various alternate embodiments. For example, in some embodiments, the cover member and base plate may be formed from a single or unitary piece in contrast to being joined together. For instance, the opening for the porous mesh member may be bored into the fluid emission side to a depth corresponding to a location of the cover member or portion of the single or unitary piece. As another example, a unitary base plate and cover unit may be formed by casting, with an opening extending through the fluid emission side to a cover region formed as part of a casting process.

Figure 6:
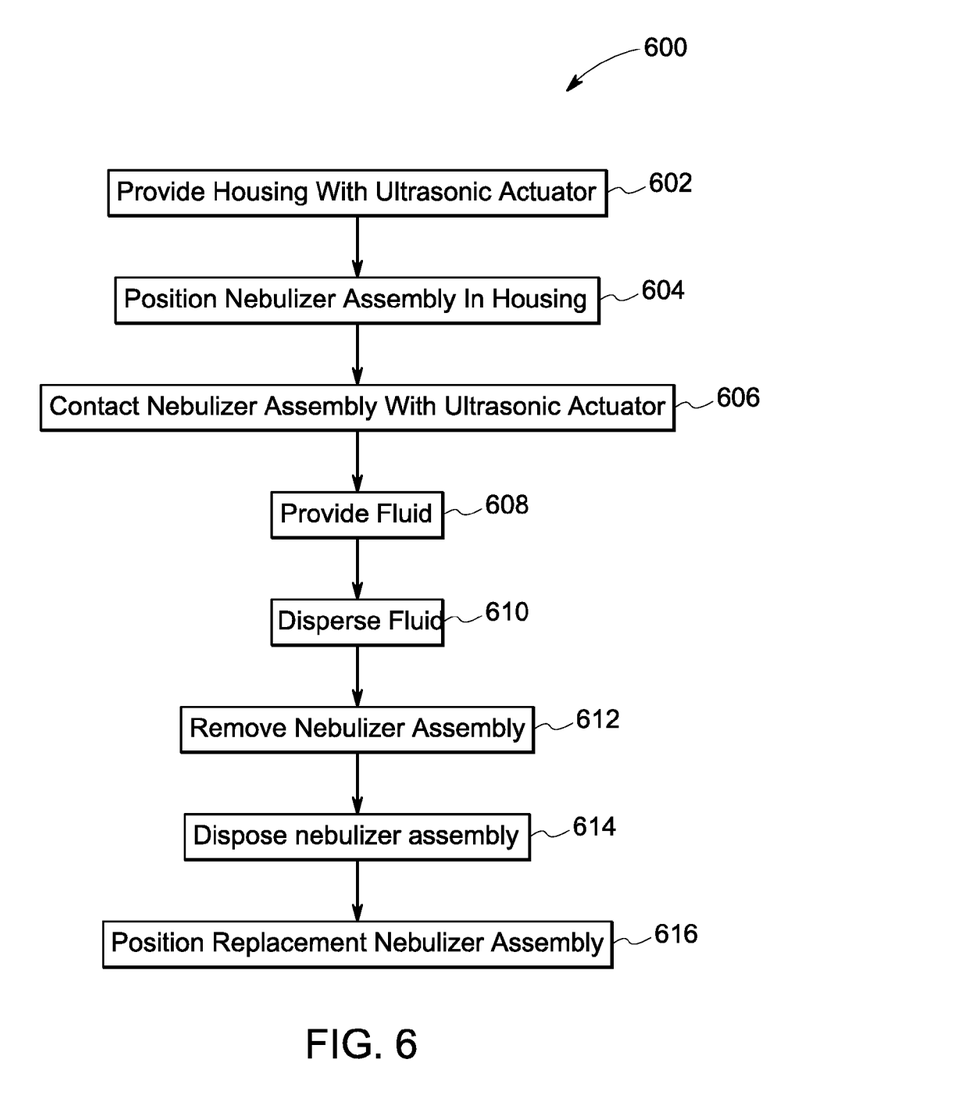
FIG. 6 is a flowchart of a method for using a nebulizer assembly in accordance with various embodiments.

FIG. 6 is a flowchart for a method 600 (e.g., a method for using a nebulizer assembly) in accordance with an embodiment. In various embodiments, the method 600, for example, may employ structures or aspects of various embodiments (e.g., systems and/or methods) discussed herein. In various embodiments, certain steps may be omitted or added, certain steps may be combined, certain steps may be performed simultaneously, certain steps may be performed concurrently, certain steps may be split into multiple steps, certain steps may be performed in a different order, or certain steps or series of steps may be re-performed in an iterative fashion.

At 602, a housing with an ultrasonic actuator is provided. The ultrasonic actuator, for example, may be a sonotrode similar to sonotrodes used in ultrasonic welding. The sonotrode in various embodiments may be permanently, semi-permanently, or releasable secured in the housing. The housing may be fixed and/or configured to be hand held. In various embodiments, the housing may be operably connected or connectable to a mouthpiece or face mask for delivery of an atomized fluid for inhalation by a patient.

At 604, a nebulizer assembly is positioned in the housing. In various embodiments, the nebulizer assembly may be inserted into an opening or slot in the housing, and/or may be inserted into the housing like a shell or cartridge. The nebulizer assembly may be retained in the housing via one or more of a clip, latch, fastener, guide, detent, or the like. In some embodiments, the nebulizer assembly may be positioned in the housing to provide for fluid connection to a fluid supply system. In other embodiments, the nebulizer assembly may be effectively sealed or otherwise self-contained, for example, the nebulizer assembly may include a predetermined dosage of a fluid to be atomized contained therein.

At 606, the nebulizer assembly is contacted with ultrasonic actuator. In some embodiments the ultrasonic actuator may be contacted when the nebulizer assembly is position at 604, while in other embodiments the nebulizer assembly may be inserted in a disengaged position having a gap between the nebulizer assembly and the ultrasonic actuator. Subsequently, one or more of the nebulizer assembly and/or the ultrasonic actuator may be actuated to an engaged position in which the ultrasonic actuator contacts the nebulizer assembly. In various embodiments, the ultrasonic actuator may be maintained in a position outside of a fluid emission region. For example, the ultrasonic actuator may be brought into contact with a surface of the nebulizer assembly disposed opposite a fluid or mist emission side of the nebulizer assembly.

At 608, a fluid to be atomized is provided to the nebulizer assembly. For example, in some embodiments, a fluid may be provided from an external reservoir or other source via a supply line and a feed-in channel to a cavity of the nebulizer assembly. The cavity may be in fluid communication with a porous mesh member of the nebulizer assembly. The fluid may be supplied, for example, from a syringe, pump, or the like. In various embodiments, a controller may receive information from sensors disposed along a fluid delivery circuit and be configured to control the operation of the fluid deliver circuit to deliver one or more of a desired volume, rate, or pressure of fluid to the cavity. In still other embodiments, the nebulizer assembly may be effectively sealed or otherwise self-contained and the fluid to be atomized may be provided in the cavity during a manufacture, assembly, or packaging process. As one example, the fluid to be atomized may be configured as an anesthetic agent. As another example, the fluid to be atomized may be a medicine. As still another example, the fluid to be atomized may be water (e.g., heated water) to be inhaled by a patient for humidification purposes.

At 610, at least a portion of the fluid in the cavity to be atomized is dispersed as an atomized or nebulized mist from the nebulizer assembly (e.g., to a patient). In various embodiments, ultrasonic energy may be provided by an ultrasonic actuator (e.g., a sonotrode) in contact with a surface of a cover member or a base plate of the nebulizer assembly, with the cover member and/or base plate configured to be substantially rigid such that the ultrasonic energy is transferred through the base plate to the porous mesh member. The ultrasonic energy transmitted to the porous mesh member may cause the porous mesh member to vibrate, resulting in the passage of droplets of the fluid to be atomized through microholes of the porous mesh member. In some embodiments, a portion of the fluid in the cavity provided for atomization may be removed from the cavity via a feed-out channel or vent, for example, to reduce a pressure within the cavity.

At 612, the nebulizer assembly is removed. In various embodiments, for example, the ultrasonic actuator (e.g., sonotrode) may be retracted to a disengaged position, and the nebulizer assembly removed from the housing. For example, a latch, clip, or the like retaining the nebulizer assembly in place may be released to allow removal of the nebulizer assembly. In other embodiments, the nebulizer assembly may be removed while the nebulizer assembly and ultrasonic actuator are in an engaged position (e.g., as the nebulizer assembly and ultrasonic actuator are not affixed, adhered, or otherwise mounted to each other, they may be readily brought out of contact, for example, via a sliding motion).

At 614, the nebulizer assembly removed at 612 may be disposed. In various embodiments, the nebulizer assembly is devoid of any sensors, detectors, ultrasonic acutators such as piezoelectric devices, or the like adhered, affixed, or otherwise mounted to the nebulizer assembly, providing for a low cost nebulizer assembly unit that may be easily and cost effectively be disposed.

At 616, a replacement nebulizer assembly is positioned, for example in a similar mounting portion of a housing used for positioning the previous nebulizer assembly at 604. A replacement nebulizer may be utilized, for example, to provide an additional dosage, to provide a dosage of a different fluid to be atomized, to provide a different type of nebulization (e.g., rate of delivery or fluid to be delivered), to provide nebulization at a subsequent time, or the like. After the replacement nebulizer assembly is positioned, in various embodiments the method may return to 606.

It should be noted that the particular arrangement of components (e.g., the number, types, placement, or the like) of the illustrated embodiments may be modified in various alternate embodiments. In various embodiments, different numbers of a given module or unit may be employed, a different type or types of a given module or unit may be employed, a number of modules or units may be combined, a given module or unit may be divided into plural modules (or sub-modules) or units (or sub-units), a given module or unit may be added, or a given module or unit may be omitted.

Thus, various embodiments provide for improved control and/or consistency of delivery of fluid in nebulizer systems. Various embodiments may also provide for more precise dosage control. Various embodiments reduce the amount of dead volume associated with a vibrating mesh or membrane, and provide reduced waste of a fluid and improved consistency in operating conditions (e.g., pressure, volume, flow rate) of the fluid. Various embodiments provide for the remote (e.g., not in direct contact with a mesh or membrane, at a substantial distance away from a mesh or membrane, and/or removed from a fluid path of a fluid that has been nebulized or is to be nebulized) sensing of operation of a nebulizer, for example rate of mist delivery. Additionally or alternatively, various embodiments provide one or more nebulizer assemblies with a releasably attachable ultrasonic actuator providing, for example, for use of a re-usable ultrasonic actuator with a plurality of disposable nebulizer assemblies. Various embodiments provide for robust and orientation free operation of a nebulizer assembly. Also, various embodiments provide low cost disposable nebulizer assemblies (e.g., assemblies that do not result in the disposal of sensors and/or piezoelectric devices affixed thereto).

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. Dimensions, types of materials, orientations of the various components, and the number and positions of the various components described herein are intended to define parameters of certain embodiments, and are by no means limiting and are merely exemplary embodiments. Many other embodiments and modifications within the spirit and scope of the claims will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the various embodiments, and also to enable a person having ordinary skill in the art to practice the various embodiments, including making and using any devices or systems and performing any incorporated methods. The patentable scope of the various embodiments is defined by the claims, and may include other examples that occur to those skilled in the art. Such other examples are intended to be within the scope of the claims if the examples have structural elements that do not differ from the literal language of the claims, or the examples include equivalent structural elements with insubstantial differences from the literal languages of the claims.

What is claimed is:

1. A nebulizer assembly comprising:
   a base plate portion having an opening extending therethrough, the base plate portion configured to transmit ultrasonic vibrations from an ultrasonic actuator through the base plate portion;
   a porous mesh member configured for passage therethrough of a nebulized fluid, the porous mesh member disposed in the opening of the base plate portion proximate a fluid emission side of the nebulizer assembly, the porous mesh member configured to receive the ultrasonic vibrations from the ultrasonic actuator via the base plate portion, wherein the ultrasonic vibrations received by the porous mesh member via the base plate portion cause the porous mesh member to vibrate and pass droplets through the vibrating porous mesh member; and
   a cover member disposed on a second side of the nebulizer assembly opposite the fluid emission side, the cover member covering the opening and defining a cavity within the base plate portion between the cover member and the porous mesh member, the cavity configured to retain a fluid to be nebulized, the cover member configured to receive the ultrasonic vibrations from the ultrasonic actuator and to transmit the ultrasonic vibrations to the base plate portion.

2. The nebulizer assembly of claim 1, wherein the second side disposed opposite the fluid emission side is configured as an actuator side, wherein the actuator side is configured for contact with the ultrasonic actuator, wherein the ultrasonic actuator contacts the cover member but is not in contact with or in a path of the fluid to be nebulized.

3. The nebulizer assembly of claim 2, wherein the cover member covers less than an entirety of the base plate portion proximate the actuator side, and wherein the base plate portion comprises an exposed portion configured for contact with the ultrasonic actuator.

4. The nebulizer assembly of claim 1, wherein the cavity comprises an effectively sealed cavity configured to contain a predetermined dosage of a medicine, wherein the nebulizer assembly is configured as a self-contained disposable unit.

5. The nebulizer assembly of claim 1, further comprising a feed-in channel in fluid communication with the cavity, the feed-in channel configured to provide a pathway for fluid supply from outside of the nebulizer assembly to the cavity.

6. The nebulizer assembly of claim 5, further comprising a feed-out channel in fluid communication with the cavity, the feed-out channel configured to provide a pathway for fluid extraction from the cavity to outside of the nebulizer assembly.

7. The nebulizer assembly of claim 5, wherein at least a portion of the feed-in channel is formed in at least one of the base plate portion and the cover member.

8. The nebulizer assembly of claim 1, wherein the cover member is friction welded to the base plate portion.

9. A system comprising:
   an ultrasonic actuator mounting portion, the ultrasonic actuator mounting portion configured to secure a sonotrode in a desired position;
   a nebulizer assembly mounting portion, the nebulizer assembly mounting portion configured to releaseably accept a nebulizer assembly comprising a base plate portion, a porous mesh member, and a cover member, the base plate portion comprising an opening in which the porous mesh member is disposed proximate a fluid emission side, the cover member covering the opening proximate an actuator side wherein a cavity for retaining a fluid to be nebulized is defined within the base plate portion between the cover member and the porous mesh member;
   wherein the sonotrode, when in the desired position, contacts the nebulizer assembly, when the nebulizer assembly is positioned in the nebulizer assembly mounting portion, such that ultrasonic vibrations from the sonotrode are configured to pass through the base plate portion to the porous mesh member to vibrate the porous mesh member, wherein the sonotrode contacts the nebulizer assembly on an actuator side opposite a fluid emission side such that the sonotrode contacts the nebulizer assembly but is not in contact with or in a path of the fluid to be nebulized.

10. The system of claim 9, wherein the nebulizer assembly includes a feed-in channel in fluid communication with the cavity, the system further comprising a pressure delivery module configured to provide the fluid to be nebulized to the cavity via the feed-in channel.

11. The system of claim 10, wherein the nebulizer assembly includes a feed-out channel in fluid communication with the cavity, wherein the system includes a fluid delivery circuit configured to include the feed-in channel and the feed-out channel when the nebulizer assembly is positioned in the nebulizer mounting portion, wherein fluid removed from the nebulizer assembly via the feed-out channel may be returned to the nebulizer assembly via the feed-in channel.

12. The system of claim 9, wherein the nebulizer assembly is configured as an effectively sealed assembly having a predetermined dose of medicine.

13. A method of providing a nebulizer assembly comprising:
   providing a base plate having an opening extending therethrough, the base plate comprising a fluid emission side and a second side, the second side disposed opposite the fluid emission side, the base plate configured to transmit ultrasonic vibrations from an ultrasonic actuator through the base plate;

securing a porous mesh member configured for ultrasonic nebulization in the opening proximate the fluid emission side, the porous mesh member configured to receive the ultrasonic vibrations from the ultrasonic actuator via the base plate; and securing a cover member to the base plate proximate the second side of the base plate with the cover member covering the opening and defining a cavity within the base plate between the cover member and the porous mesh member, the cavity configured to retain a fluid to be nebulized, the cover member configured to receive the ultrasonic vibrations from the ultrasonic actuator and to transmit the ultrasonic vibrations to the base plate, wherein the ultrasonic vibrations received by the porous mesh member via the base plate cause the porous mesh member to vibrate and pass droplets through the vibrating porous mesh member.

14. The method of claim 13, wherein the second side disposed opposite the fluid emission side is configured as an actuator side, wherein the actuator side is configured for contact with the ultrasonic actuator.

15. The method of claim 13, further comprising adding a predetermined dosage of a medicine to the opening, wherein the securing the cover member comprises securing the cover member to effectively seal the cavity with the predetermined dosage therein such that the predetermined dosage may only exit the cavity via the porous mesh member.

16. The method of claim 13, further comprising providing a feed-in channel in fluid communication with the cavity, the feed-in channel configured to provide a pathway for fluid supply from outside of the nebulizer assembly to the cavity.

17. The method of claim 16, further comprising providing a feed-out channel in fluid communication with the cavity, the feed-out channel configured to provide a pathway for fluid extraction from the cavity to outside of the nebulizer assembly.

18. The method of claim 16, wherein the providing the feed-in channel comprises forming at least a portion of the feed-in channel in at least one of the base plate and the cover member.

19. The method of claim 18, wherein the forming at least a portion of the feed-in channel in at least one of the base plate and the cover member comprises etching the at least a portion of the feed-in channel in at least one of the base plate and the cover member.

20. The method of claim 13, wherein the securing the cover member to the base plate comprises friction welding the cover member to the base plate.

* * * * *